United States Patent

Yoshikawa

[11] 4,225,534
[45] Sep. 30, 1980

[54] PROCESS FOR THE PRODUCTION OF 2-CHLOROBENZONITRILE DERIVATIVES

[75] Inventor: Hiroshi Yoshikawa, Takasaki, Japan

[73] Assignee: Nippon Kayaku Kabushiki Kaisha, Tokyo, Japan

[21] Appl. No.: 46,371

[22] Filed: Jun. 7, 1979

[30] Foreign Application Priority Data

Jun. 12, 1978 [JP] Japan ............................ 53-69836
Oct. 11, 1978 [JP] Japan ........................... 53-124875

[51] Int. Cl.² .................................. C07C 121/52
[52] U.S. Cl. ....................................... 260/465 G
[58] Field of Search ............................. 260/465 G

[56] References Cited

U.S. PATENT DOCUMENTS 3,185,725  5/1965  Koopman .................... 260/465 G
3,351,651  11/1967  Rothman .................... 260/465 G

OTHER PUBLICATIONS

Caddy, J. Chem. Soc., Perkin Trans. II, pp. 1807–1811 (1972).

Primary Examiner—Dolph H. Torrence
Attorney, Agent, or Firm—Russell & Nields

[57] ABSTRACT

A process for the production of 2-chlorobenzonitrile derivatives represented by the general formula (I):

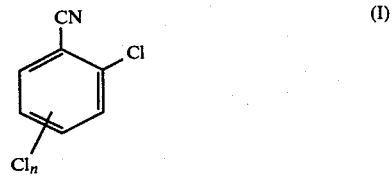

(I)

(wherein n is a number of 1 or 2)

characterized by reacting a compound of the general formula (II):

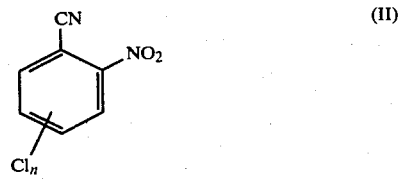

(II)

(wherein $Cl_n$ is as defined above)

with lithium chloride or a mixture of lithium chloride and anhydrous aluminum chloride or with lithium aluminum chloride in an aprotic solvent.

10 Claims, No Drawings

PROCESS FOR THE PRODUCTION OF 2-CHLOROBENZONITRILE DERIVATIVES

DETAILED DESCRIPTION OF THE INVENTION

This invention relates to a process for producing 2-chlorobenzonitrile derivatives represented by the general formula (I):

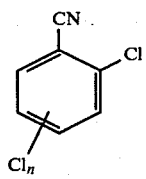

(wherein n is a number of 1 or 2)
characterized by reacting a compound of the general formula (II):

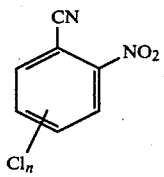

(wherein $Cl_n$ is as defined above)
with lithium chloride or a mixture of lithium chloride and anhydrous aluminum chloride or with lithium aluminum chloride in an aprotic solvent.

The compounds represented by the general formula (I) are known as the excellent agricultural chemicals and the intermediates for the preparation of other variety of useful materials.

The following methods are known for the production of 2,6-dichlorobenzonitrile from 2-chloro-6-nitrobenzonitrile: 2-chloro-6-nitrobenzonitrile is reduced into 2-chloro-6-aminobenzonitrile and the latter is subjected to a Sandmeyer reaction; and 2-chloro-6-nitrobenzonitrile is treated with chlorine gas (or a mixture thereof with hydrogen chloride gas) or thionyl chloride in a solvent such as dichlorobenzene at high temperature to substitute the nitro group with chlorine. However, the former method is troublesome since it involves many steps such as reduction, diazotization and substitution with chlorine and also releases a large volume of wastes, so that this method is not suited for industrial practice. On the other hand, the latter method uses a material which is poisonous and strongly corrosive and there is also produced nitrogen dioxide gas which is a poisonous and strongly corrosive gas, so that this method has difficulties for practical use.

The process of this invention is capable of producing the object substance with minimized generation of poisonous nitrogen dioxide and very limited release of wastes and with safety by merely reacting a compound of the formula (II) with lithium chloride or a mixture thereof with anhydrous aluminum chloride or with lithium aluminum chloride in an aprotic solvent.

In case of using a mixture of lithium chloride and anhydrous aluminum chloride or lithium aluminum chloride in the process of this invention, the formation of by-products is reduced and the object product can be obtained in a high yield.

It is considered that when a mixture of lithium chloride and anhydrous aluminum chloride is used in this invention, there is formed lithium aluminum chloride with different compositional proportions depending on the mixing ratio of lithium chloride and anhydrous aluminum chloride in the reaction system.

A lithium compound, such as lithium carbonate, which can be converted into lithium chloride in the reaction system, may be used in this invention.

Lithium in the lithium compound used in this invention can be easily recovered by mere filtration or in the form of a precipitate by adding an organic solvent such as toluene.

The compounds of the formula (II) used in this invention include 2-chloro-6-nitrobenzonitrile, 4-chloro-2-nitrobenzonitrile, 2,3-dichloro-6-nitrobenzonitrile, 4,5-dichloro-2-nitrobenzonitrile and the like.

The aprotic solvents used in this invention include N,N-dimethylformamide, dimethylsulfoxide, N,N-dimethylacetamide, hexamethylphosphoramide and N-methylpyrrolidone and the like. Dehydrated solvents are preferable. The amount of the solvent used may vary over a wide range and the preferred amount of the solvent is within the range of 0.5 to 10 times the weight of the compound of the formula (II).

The lithium compound (lithium chloride or lithium aluminum chloride) is used such that the lithium content in the lithium compound is preferably 0.1 to 20 gram atoms, more preferably 0.3 to 3 gram atoms, per mole of the compound of the formula (II).

In case of employing a mixture of lithium chloride and anhydrous aluminum chloride or lithium aluminum chloride, it is used in such a ratio that the aluminum content is preferably 0.01 to 10 atoms, more preferably 0.1 to 2 atoms, per atom of lithium.

The reaction of this invention is preferably carried out at a temperature of 120° to 220° C., more preferably at 150° to 200° C. The reaction time, although not specifically defined, is usually 0.5 to 20 hours.

The compounds of the formula (I), such as 2,6-dichloro-benzonitrile, obtained according to the process of this invention can be easily isolated by an ordinary means such as distillation, recrystallization, etc.

The invention is further described hereinbelow by way of the examples thereof. In the following descriptions of Examples, all the "parts" are by weight unless otherwise specified.

EXAMPLE A1

4.55 parts of 2-chloro-6-nitrobenzonitrile, 5.3 parts of lithium chloride and 15 parts of N,N-dimethylformamide were refluxed under heating for 2 hours. The reaction temperature was 178°–179° C. The reaction solution was cooled, added with 150 parts of toluene, agitated for 30 minutes and then filtered, and the filtrate was analyzed by gas chromatography. It contained 1.25 parts of 2,6-dichlorobenzonitrile and 2.06 parts of 2-chloro-6-nitrobenzonitrile.

EXAMPLE A2

4.55 parts of 2-chloro-6-nitrobenzonitrile, 2.12 parts of lithium chloride and 15 parts of N,N-dimethylformamide were refluxed under heating for 2 hours. The reaction temperature was 169°–170° C. The reaction solution was treated similarly to EXAMPLE A1 and analyzed by gas chromatography, finding 1.27 parts of 2,6-dichlorobenzonitrile and 1.84 parts of 2-chloro-6-nitrobenzonitrile in the reaction solution.

EXAMPLE A3

4.55 parts of 2-chloro-6-nitrobenzonitrile, 1.06 parts of lithium chloride and 15 parts of N,N-dimethylformamide were refluxed under heating for 2 hours. The reaction temperature was 163°–164° C. The reaction solution was treated after the manner of EXAMPLE A1 and analyzed by gas chromatography. It contained 1.14 parts of 2,6-dichlorobenzonitrile and 1.96 parts of 2-chloro-6-nitrobenzonitrile.

EXAMPLE A4

4.55 parts of 2-chloro-6-nitrobenzonitrile, 1.06 parts of lithium chloride and 15 parts of N,N-dimethylformamide were refluxed under heating for 3 hours, and the reaction solution was treated similarly to EXAMPLE A1 and analyzed by gas chromatography, finding 1.29 parts of 2,6-dichlorobenzonitrile and 1.45 parts of 2-chloro-6-nitrobenzonitrile.

EXAMPLE A5

4.55 parts of 2-chloro-6-nitrobenzonitrile, 5.3 parts of lithium chloride and 5 parts of N,N-dimethylformamide were mixed and reacted at 180° C. for 2 hours, and the reaction solution was treated same as EXAMPLE A1 and then subjected to a gas chromatographic analysis. It contained 1.05 parts of 2,6-dichlorobenzonitrile and 2.46 parts of 2-chloro-6-nitrobenzonitrile.

EXAMPLES B1–B8

4.55 parts of 2-chloro-6-nitrobenzonitrile and specified quantities (shown in Table 1) of lithium chloride (LiCl), anhydrous aluminum chloride (AlCl$_3$) and N,N-dimethylformamide (DMF) were put into a 100-ml four-necked flask and refluxed under heating at about 165° C. for a predetermined period of time. The reaction solution was cooled, added with 150 parts of toluene, agitated for 30 minutes and then filtered, and the filtrate was analyzed by gas chromatography. The reaction results were as shown in Table 1 below.

EXAMPLE B9

4.55 parts of 2-chloro-6-nitrobenzonitrile, 1.06 parts of lithium chloride, 0.53 parts of anhydrous aluminum chloride and 15 parts of N,N-dimethylformamide were refluxed under heating in a 100-ml four-necked flask. The reaction temperature was 164° C. After continuing the reaction for 3 hours, the internal temperature was lowered to 100° C. and 0.22 parts of anhydrous aluminum chloride was further added in the reaction solution and again refluxed under heating for 3 hours. Anhydrous aluminum chloride was likewise added three times thereafter, 0.11 part each time, refluxing the mixture under heating for 3 hours after each addition, and the resultant reaction solution was treated similarly to EXAMPLE B1 and analyzed by gas chromatography, finding 3.28 parts of 2,6-dichlorobenzonitrile and 0.08 parts of 2-chloro-6-nitrobenzonitrile. Conversion: 97.9%; yeild: 77.1%; selectivity: 78.8%.

EXAMPLE B10

4.55 parts of 2-chloro-6-nitrobenzonitrile, 15 parts of N-methyl-2-pyrrolidone and specified quantities (shown in Table 2) of lithium chloride and anhydrous aluminum chloride were mixed and the mixtures were reacted at various reaction temperatures. Each reaction solution was treated after the manner of EXAMPLE B1 and analyzed by gas chromatography. The reaction results were as shown in Table 2 below.

TABLE 2

| LiCl (parts) | AlCl$_3$ (parts) | Reaction temp. (°C.) | Reaction time (hr) | Conversion of 2-chloro-6-nitrobenzo-nitrile (%) | Yield of 2,6-dichloro-benzonitrile (%) | Selectivity to 2,6-dichloro-benzonitrile (%) |
|---|---|---|---|---|---|---|
| 0.42 | 1.11 | 170 | 12 | 98.7 | 89.4 | 90.6 |
| 0.42 | 1.11 | 180 | 6 | 98.2 | 89.6 | 91.2 |
| 0.42 | 1.11 | 190 | 3 | 98.0 | 88.3 | 90.1 |
| 0.35 | 1.11 | 170 | 14 | 97.6 | 86.2 | 88.4 |

EXAMPLE B11

4.55 parts of 2-chloro-6-nitrobenzonitrile, 0.92 parts of lithium carbonate, 2.78 parts of anhydrous aluminum chloride and 15 parts of N-methyl-2-pyrrolidone were put into a 100-ml four-necked flask and heated, whereby carbon dioxide gas was evolved. The mixture was reacted at 180° C. for 2.5 hours and the reaction solution was cooled, added with 100 parts of dichloroethane, agitated for 30 minutes and then filtered, and the filtrate was analyzed by gas chromatography, disclosing conversion of 2-chloro-6-nitrobenzonitrile of 98.0%, yield

TABLE 1

| Example No. | LiCl (parts) | AlCl$_3$ (parts) | DMF (parts) | Reaction time (hr) | Conversion of 2-chloro-6-nitro-benzonitrile (%) | Yield of 2,6-dichloro-benzo-nitrile (%) | Selectivity to 2,6-dichloro-benzonitrile (%) |
|---|---|---|---|---|---|---|---|
| B1 | 1.06 | 0.56 | 15 | 3 | 41.0 | 38.9 | 94.9 |
| B2 | 1.06 | 0.56 | 15 | 4 | 59.6 | 52.9 | 88.8 |
| B3 | 1.06 | 1.11 | 15 | 4 | 53.7 | 49.0 | 91.3 |
| B4 | 1.06 | 1.11 | 15 | 8 | 66.0 | 56.7 | 85.9 |
| B5 | 1.06 | 1.11 | 10 | 8 | 79.7 | 60.4 | 75.8 |
| B6 | 0.53 | 0.56 | 15 | 5 | 51.5 | 46.5 | 90.3 |
| B7 | 0.53 | 0.56 | 15 | 7 | 64.9 | 55.9 | 86.1 |
| B8 | 0.22 | 0.56 | 15 | 8 | 46.5 | 33.9 | 72.9 | of 2,6-dichlorobenzonitrile of 85.8% and selectivity to 2,6-dichlorobenzonitrile of 87.2%.

EXAMPLE B12

4.55 parts of 4-chloro-2-nitrobenzonitrile, 0.42 parts of lithium chloride, 1.11 parts of anhydrous aluminum chloride and 15 parts of N-methyl-2-pyrrolidone were reacted at 180° C. for 3 hours after the pattern of EXAMPLE B1. The reaction solution was added with 100 parts of dichloroethane, agitated for 30 minutes and filtered. Dichloroethane was distilled off from the filtrate and the residue was added with water to precipitate the crude crystals. The crude crystals were recrystallized by using a water-methanol mixed solvent to obtain 3.4 parts of 2,4-dichlorobenzonitrile with purity of 99%. Yield: 79.2%.

EXAMPLE B13

10.9 parts of 2,3-dichloro-6-nitrobenzonitrile, 0.84 parts of lithium chloride, 2.22 parts of anhydrous aluminum chloride and 15 parts of N-methyl-2-pyrrolidone were reacted at 180° C. for one hour, and the reaction solution was treated similarly to EXAMPLE B12 to obtain 9.4 parts of 2,3,6-trichlorobenzonitrile with purity of almost 100%. Yield: 91.9%.

EXAMPLE B14

A mixture of 0.84 parts of lithium chloride, 2.22 parts of anhydrous aluminum chloride and 50 parts of toluene was refluxed under heating for 30 minutes to produce lithium aluminum chloride, and the resultant mixture was added with 9.13 parts of 2-chloro-6-nitrobenzonitrile and 20 parts of N-methyl-2-pyrrolidone. After distilling off toluene, the mixture was reacted at 180° C. for 8 hours. The reaction solution was treated in the same way as EXAMPLE B1 and analyzed by gas chromatography, obtaining the following results: Conversion of 2-chloro-6-nitrobenzonitrile: 98.0%; Yield of 2,6-dichlorobenzonitrile: 87.3%; Selectivity to 2,6-dichloro-benzonitrile: 89.1%.

What is claimed is:

1. A process for producing 2-chlorobenzonitrile derivatives represented by the general formula (I):

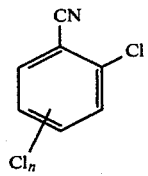

(wherein n is a number of 1 or 2) characterized by reacting a compound of the general formula (II):

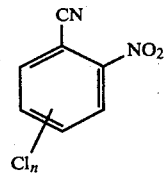

(wherein $Cl_n$ is as defined above) with lithium chloride or a mixture of lithium chloride and anhydrous aluminum chloride or with lithium aluminum chloride in aprotic solvent.

2. The process according to claim 1, wherein the compound of the formula (II) is 2-chloro-6-nitrobenzonitrile.

3. The process according to claim 1, wherein the compound of the formula (II) is 4-chloro-2-nitrobenzonitrile.

4. The process according to claim 1, wherein the compound of the formula (II) is 2,3-dichloro-6-nitrobenzonitrile.

5. The process according to claim 1, wherein the compound of the formula (II) is 4,5-dichloro-2-nitrobenzonitrile.

6. The process according to claim 1, wherein the compound of the formula (II) is reacted with lithium chloride.

7. The process according to claim 1, wherein the compound of the formula (II) is reacted with a mixture of lithium chloride and anhydrous aluminum chloride.

8. The process according to claim 1, wherein the compound of the formula (II) is reacted with lithium aluminum chloride.

9. The process according to claim 2, wherein the compound of the formula (II) is reacted with a mixture of lithium chloride and anhydrous aluminum chloride.

10. The process according to claim 2, wherein the compound of the formula (II) is reacted with lithium aluminum chloride.

* * * * *